US008969085B2

(12) United States Patent
Sharpe et al.

(10) Patent No.: US 8,969,085 B2
(45) Date of Patent: Mar. 3, 2015

(54) PORTABLE NANOPARTICLE BASED ASSAY FOR RAPID DETECTION OF FOOD ANTIOXIDANTS (NANOCERAC)

(71) Applicants: Erica Sharpe, Queensbury, NY (US); Emanuela Silvana Andreescu, Potsdam, NY (US); Daniel Andreescu, Potsdam, NY (US)

(72) Inventors: Erica Sharpe, Queensbury, NY (US); Emanuela Silvana Andreescu, Potsdam, NY (US); Daniel Andreescu, Potsdam, NY (US)

(73) Assignee: Clarkson University, Potsdam, NY (US)

( * ) Notice: Subject to any disclaimer, the term of this patent is extended or adjusted under 35 U.S.C. 154(b) by 0 days.

(21) Appl. No.: 13/971,377

(22) Filed: Aug. 20, 2013

(65) Prior Publication Data

US 2014/0162368 A1 Jun. 12, 2014

Related U.S. Application Data

(63) Continuation-in-part of application No. 13/156,755, filed on Jun. 9, 2011, now Pat. No. 8,691,520.

(60) Provisional application No. 61/684,934, filed on Aug. 20, 2012.

(51) Int. Cl.
*G01N 33/02* (2006.01)
*G01N 21/78* (2006.01)
*G01N 33/58* (2006.01)
*C12Q 1/26* (2006.01)
*G01N 33/18* (2006.01)
*G01N 21/84* (2006.01)

(52) U.S. Cl.
CPC .............. *G01N 33/02* (2013.01); *G01N 33/587* (2013.01); *C12Q 1/26* (2013.01); *G01N 33/1826* (2013.01); *G01N 21/78* (2013.01); *G01N 21/8483* (2013.01); *G01N 33/18* (2013.01)
USPC ............... 436/20; 436/82; 436/164; 436/165; 422/400; 422/430

(58) Field of Classification Search
USPC .............. 436/20, 82, 164, 165, 169; 422/400, 422/420, 68.1, 430
See application file for complete search history.

(56) References Cited

U.S. PATENT DOCUMENTS 3,721,607 A 3/1973 Gruber et al.
7,504,356 B1 3/2009 Self et al.
2009/0071848 A1 3/2009 Seal et al.

FOREIGN PATENT DOCUMENTS

JP 2011017663 1/2011
WO 2006130473 7/2006
WO WO2007034284 3/2007

OTHER PUBLICATIONS

Ornatska et al. Abstract from the 37th Northeast Regional Meeting of the American Chemical Society, Potsdam, NY, United States, Jun. 2-5, 2010.*
Ozyurt et al. Journal of Fluorescence, vol. 21, 2011, pp. 2069-2076.*
Ozyurt et al. Journal of Food Composition and Analysis, vol. 23, 2010, pp. 282-288.*
Patil, S. D., Fundamental Aspects of Regenerative Cerium Oxide Nanoparticles and Their Applications in Nanobiotechnology (Ph.D. Thesis), University of Central Florida, Orlando, 2006, pp. 1-126.
Ornatska, M. et al., Paper Bioassay Based on Ceria Nanopoarticles as Colorimetric Probes, Analytical Chemistry, Apr. 28, 2011, vol. 83, pp. 4273-4280.
International Search Report Form PCT/ISA/220, International Application No. PCT/2012/041608, pp. 1-12, Dated Dec. 24, 2012.
Babko, A. K. and Volkova, A. I., 1954, "The Colored Peroxide Complex of Cerium", Ukrains'kii Khemichnii Zhurna 20: pp. 211-215.
Beach, E. F. and Turner, J. J., 1958, "An Enzymatic Method for Glucose Determination in Body Fluids", Clinical Chemistry 4(6); pp. 462-475.
Dungchai, W., Chailapakul, O., et al., 2010, "Use of Multiple Colorimetric Indicators for Paper-based Microfluidic Devices", Analytica Chimica Acta, 674(2): pp. 227-233.
Ispas, C., Njagi, J., et al., 2008, "Electrochemical Studies of Ceria as Electrode Material for Sensing and Biosensing Applications," Journal of the Electrochemical Society 155(8): pp. F169-F176.
Martinez, A., Phillips, S., et al., 2007, "Patterned Paper as a Platform for Inexpensive, Low-Volume, Portable Bioassays", Angewandte Chemie International Edition 46(8): pp. 1318-1320.
Mehta, A., Patil, S., et al., 2007, "A Novel Multivalent Nanomaterial Based Hydrogen Peroxide Sensor", Sensors and Actuators a-Physical 134(1): pp. 146-151.
Trinder, P., 1969, "Determination of Blood Glucose Using 4-Amino Phenazone as Oxygen Acceptor", Journal of Clinical Pathology 22(2): p. 246.
Yu, P., Hayes, S. A., et al., 2006, "The Phase Stability of Cerium Species in Aqueous Systems—II. The Ce(III/IV)-H2O—H2O2/O-2 Systems. Equilibrium Considerations and Pourbaix Diagram Calculations", Journal of the Electrochemical Society 153(1): pp. C74-C79.
Barnard et al., Infection and Immunity, vol. 67, No. 12, pp. 6558-6564, Dec. 1999.
International Search Report Form PCT/ISA/220, International Application No. PCT/US2013/055778, pp. 1-11, dated Nov. 18, 2013.

* cited by examiner

*Primary Examiner* — Maureen Wallenhorst
(74) *Attorney, Agent, or Firm* — George R. McGuire; Daniel P. Malley; Bond Schoeneck & King, PLLC

(57) ABSTRACT

Methods and assay for the portable colorimetric detection of an antioxidant in a food sample. The method includes the steps of providing a colorimetric reagent, the reagent including a plurality of ceria nanoparticles immobilized to a support, contacting the colorimetric reagent with the food sample, and detecting an optical property of the colorimetric reagent, where a change in the optical property of the colorimetric reagent is associated with the presence of antioxidant in the food sample. The change in the optical property of the colorimetric reagent is dependent upon the concentration of the antioxidant in the food sample.

19 Claims, 8 Drawing Sheets

| Tea Type | Sensor response to sample addition (g/L) | Sensitivity (slope of CI vs conc g/L) | GAE (mmol GA/g sample) | ORAC (mmol Trolox/g sample) |
|---|---|---|---|---|
| Rooibos *Aspalathus linearus* | 0.08　0.14　0.6　1.3　2.6　5.1 | 86.149 | 0.98 | 1 |
| White Tea *Camellia Sinensis* | 0.2　0.3　0.23　0.38　0.63　1.06　1.76　2.93 | 64.421 | 0.73 | 1.5 |
| Green Tea *Camellia Sinensis* | 0.5　0.8　1.4　2.3　3.9　6.5　10.8 | 58.348 | 0.66 | 1.4 |
| Black Tea *Camellia Sinensis* | 0.2　0.4　0.8　1.6　3.1　6.2 | 57.643 | 0.65 | 1.8 |

FIG. 9

PORTABLE NANOPARTICLE BASED ASSAY FOR RAPID DETECTION OF FOOD ANTIOXIDANTS (NANOCERAC)

CROSS-REFERENCE TO RELATED APPLICATIONS

This application claims priority to U.S. patent application Ser. No. 13/156,755, filed on Jun. 9, 2011 and entitled "Reagentless Ceria-Based Colorimetric Sensor," now U.S. Pat. No. 8,691,520, and to U.S. Provisional Patent Application Ser. No. 61/684,934, filed on Aug. 20, 2012 and entitled "Portable Nanoparticle Based Assay For Rapid Detection of Food Antioxidants (NanoCerac)," the entire disclosures of which are incorporated herein by reference.

BACKGROUND

The present invention relates to methods and assays for antioxidant detection and, more specifically, to methods and assays that reliably measure the antioxidant capacity of dietary products.

In recent years, much attention has been drawn to antioxidants because of their supposed ability to fight cancer, promote health and prevent a wide variety of diseases including heart disease, aging, and neurodegenerative diseases such as Parkinson's and Alzheimer's. Scientific knowledge and epidemiological evidence suggest that consumption of antioxidant compounds reduces oxidative stress created by reactive oxygen and nitrogen species ("ROS" and "RNS"), and thus provides prophylactic and therapeutic benefits in the treatment of disease. However, the true antioxidant capacity of any given compound and dietary food product is questionable. A current limitation is the lack of validated assays that can reliably and accurately measure antioxidant capacity. Conventional antioxidant assays involve the use of radical generation systems, colorimetric dyes, fluorophores or enzymes, and require spectroscopic or electrochemical instrumentation. In general, these assays are not portable and their cost is prohibitive for general use. Additionally, all of these assays determine antioxidant capacity in a controlled laboratory environment.

Most antioxidant activity assays currently in practice assess the ability of an antioxidant to scavenge synthetically created free radicals (e.g. ROS, RNS) or to reduce reactive redox metals (e.g. iron, copper or gold). Some assays assess the ability of an antioxidant to scavenge a specific radical (e.g. $ABTS.^+$ (2,2'-azino-bis(3-ethylbenzothiazoline-6-sulphonic acid), DPPH. (1,1-diphenyl-2-picrylhydrazyl), superoxide ($O_2.^-$), while others provide a total antioxidant/reducing capacity. Examples of commonly used assays include the ORAC (oxygen radical absorbance capacity) and the TRAP (total radical trapping antioxidant parameter) assays which use fluorescence to test the ability of a compound to neutralize peroxyl radicals. Assays designed to reduce redox metals involve iron, copper and gold reduction. For example, the FRAP (ferric reducing antioxidant power) assay monitors the ability of an antioxidant to reduce Fe(III) to Fe(II) and the CUPRAC (copper reduction antioxidant assay) monitors the ability of an antioxidant to reduce Cu(III) to Cu(II). Each of these assays assess the ability of a compound to interact with one unique ROS (DPPH, $ABTS.^+$, DPPH., superoxide $O_2.^-$, $H_2O_2$) or a redox metal (Fe, Au, or Cu) and reveal different specificities toward free radicals. Therefore each assay ranks antioxidants in a different order of hierarchy and most inter-assay comparisons show significant discrepancies, and thus a questionable ranking of the antioxidant power. Most often, the use of multiple, complementary assays is needed to gain a complete understanding of the total antioxidant activity. At present there are no portable antioxidant assays suited for field use. Accordingly, there is a continued demand for simple, easy-to-use tests that can reliably measure the antioxidant capacity of dietary products. Further, there is a continued demand for antioxidant sensing tests that do not require specialized equipment and which can be utilized for high-throughput analysis of a large number of assays.

BRIEF SUMMARY

Systems and methods for colorimetric detection of an antioxidant in a food sample. According to one aspect is a method for the portable colorimetric detection of an antioxidant in a food sample, the method comprising the steps of: (i) providing a colorimetric reagent comprising a plurality of ceria nanoparticles immobilized to a support; (ii) contacting the colorimetric reagent with the food sample; and (iii) detecting an optical property of the colorimetric reagent, wherein a change in the optical property of the colorimetric reagent is associated with the presence of antioxidant in the food sample, and further wherein the change in the optical property of the colorimetric reagent is dependent upon the concentration of the antioxidant in said food sample.

According to another aspect, the concentration-dependent change in the optical property of the colorimetric reagent is associated with a concentration of approximately 20-400 µM of said antioxidant.

According to yet another aspect, the plurality of ceria nanoparticles comprise cerium oxide.

According to one aspect, the method further comprises the step of reusing the colorimetric reagent.

According to another aspect, the plurality of ceria nanoparticles comprise cerium (IV), and further wherein said change in the optical property of the colorimetric reagent is caused by the reduction of said cerium (IV) to cerium (III) caused by the antioxidant in said sample.

According to another aspect, the colorimetric reagent further comprises a plurality of peroxyl radicals.

According to an aspect, the method further comprises the step of comparing the optical property of the colorimetric reagent to a pre-determined value.

According to one aspect is a method for the portable colorimetric detection of an antioxidant in a food sample, the method comprising the steps of: (i) providing a colorimetric reagent comprising a plurality of ceria nanoparticles immobilized to a support, the plurality of ceria nanoparticles comprising cerium oxide; (ii) contacting the colorimetric reagent with the food sample; (iii) detecting an optical property of the colorimetric reagent, wherein a change in the optical property of the colorimetric reagent is associated with the presence of antioxidant in the food sample, and further wherein the change in the optical property of the colorimetric reagent is dependent upon the concentration of the antioxidant in said food sample; and (iv) comparing the optical property of the colorimetric reagent to a pre-determined value.

According to another aspect is an assay for the portable colorimetric detection of an antioxidant in a food sample, the assay comprising a colorimetric reagent comprising a plurality of ceria nanoparticles immobilized to a support, wherein the colorimetric reagent comprises an optical property, and further wherein a change in the optical property of the colorimetric reagent is associated with the presence of antioxidant in the food sample, and further wherein the change in the optical property of the colorimetric reagent is dependent upon the concentration of the antioxidant in said food sample.

According to one aspect of the assay, the concentration-dependent change in the optical property of the colorimetric reagent is associated with a concentration of approximately 20-400 μM of said antioxidant.

According to another aspect of the assay, the plurality of ceria nanoparticles comprise cerium oxide.

According to yet another aspect, the colorimetric reagent can be reused for multiple assays.

According to an aspect of the assay, the plurality of ceria nanoparticles comprise cerium (IV), and further wherein said change in the optical property of the colorimetric reagent is caused by the reduction of said cerium (IV) to cerium (III) caused by the antioxidant in said sample.

According to another aspect of the assay, the colorimetric reagent further comprises a plurality of peroxyl radicals.

According to one aspect, the assay further comprises means for comparing the optical property of the colorimetric reagent to a pre-determined value.

According to an aspect is a system for the portable colorimetric detection of an antioxidant in a food sample, the system comprising: (i) a food sample; and (ii) a colorimetric reagent comprising a plurality of ceria nanoparticles immobilized to a support, wherein the colorimetric reagent comprises an optical property, and further wherein a change in the optical property of the colorimetric reagent is associated with the presence of antioxidant in the food sample, and further wherein the change in the optical property of the colorimetric reagent is dependent upon the concentration of the antioxidant in said food sample.

According to one aspect of the system, the concentration-dependent change in the optical property of the colorimetric reagent is associated with a concentration of approximately 20-400 μM of said antioxidant.

According to another aspect of the system, the plurality of ceria nanoparticles comprise cerium oxide.

According to yet another aspect of the system, the plurality of ceria nanoparticles comprise cerium (IV), and further wherein said change in the optical property of the colorimetric reagent is caused by the reduction of said cerium (IV) to cerium (III) caused by the antioxidant in said sample.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4:
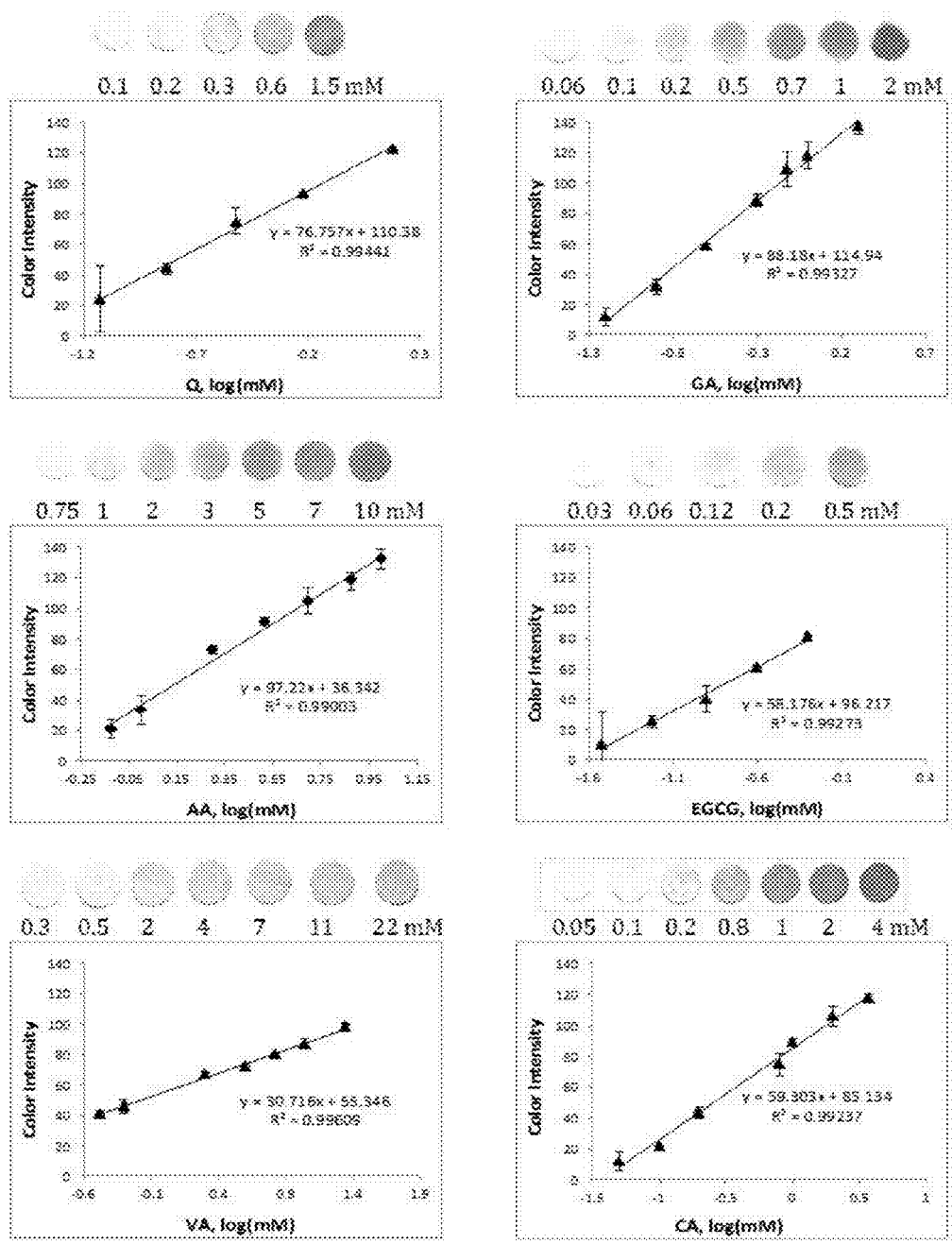
Figure 5:
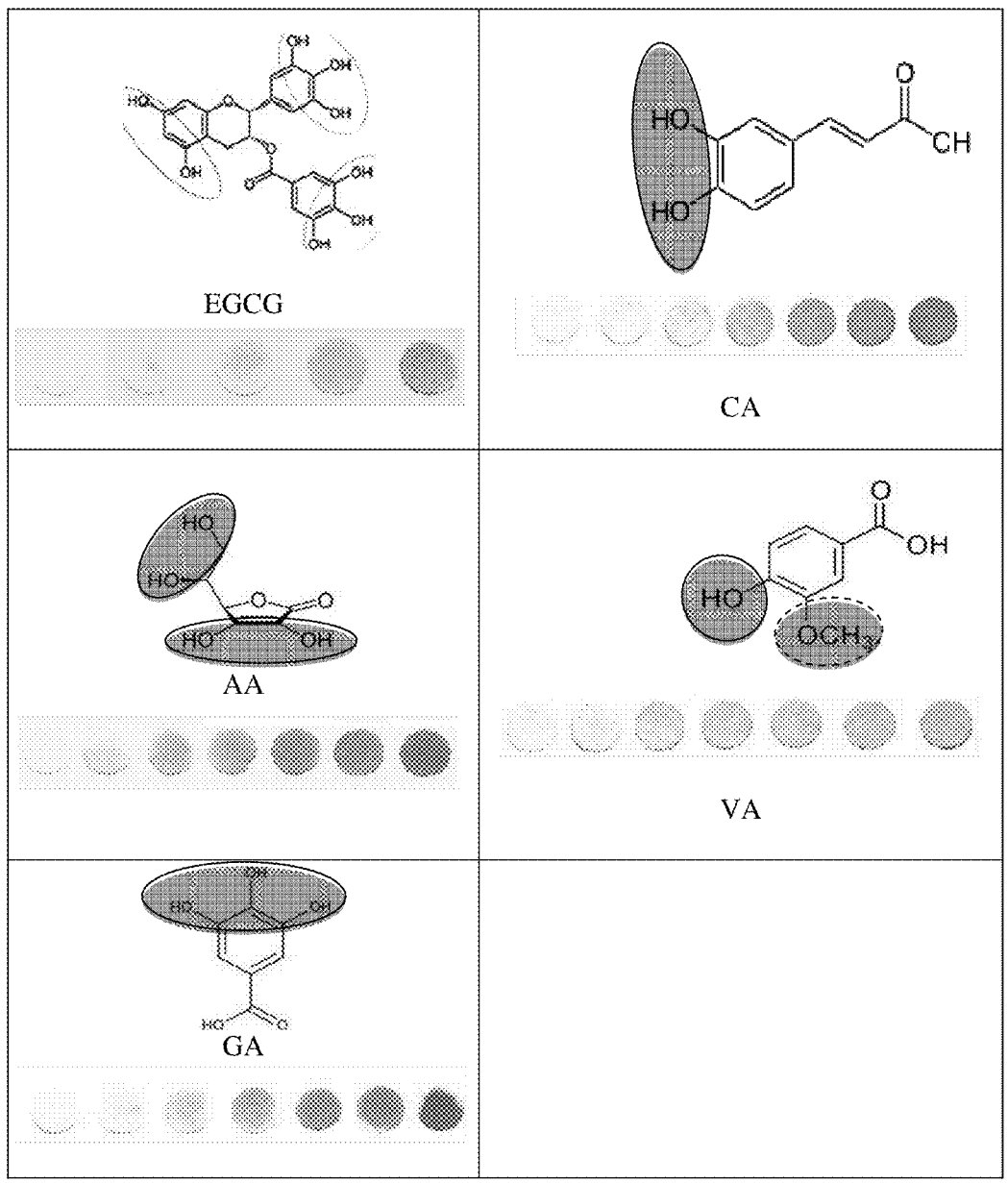
Figure 6:
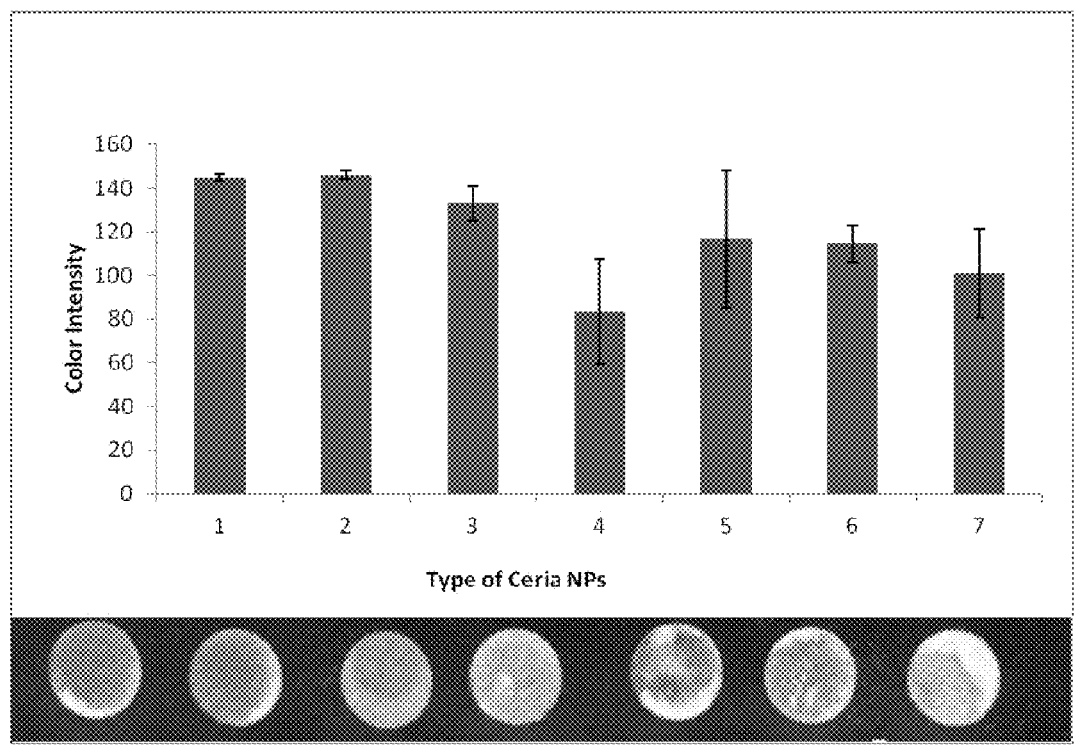
Figure 7:
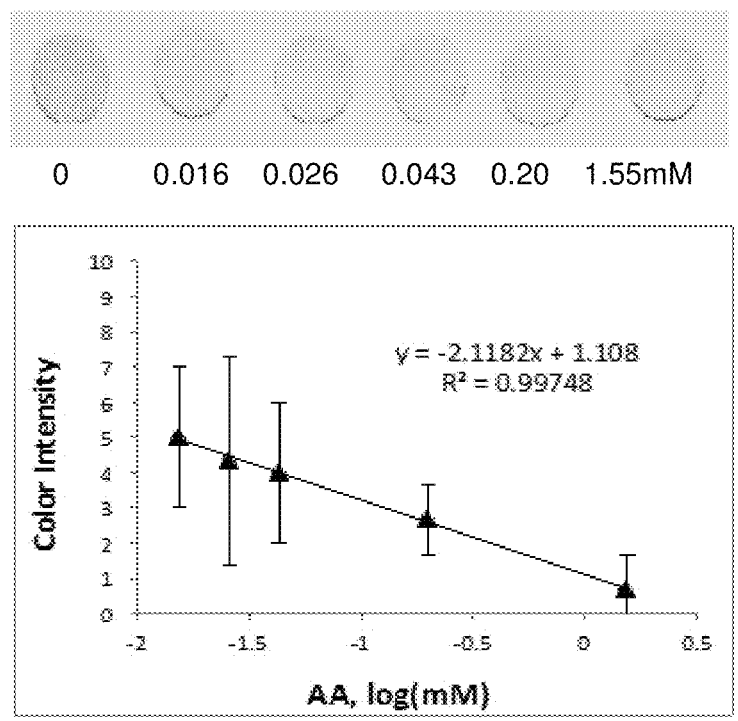
Figure 8:
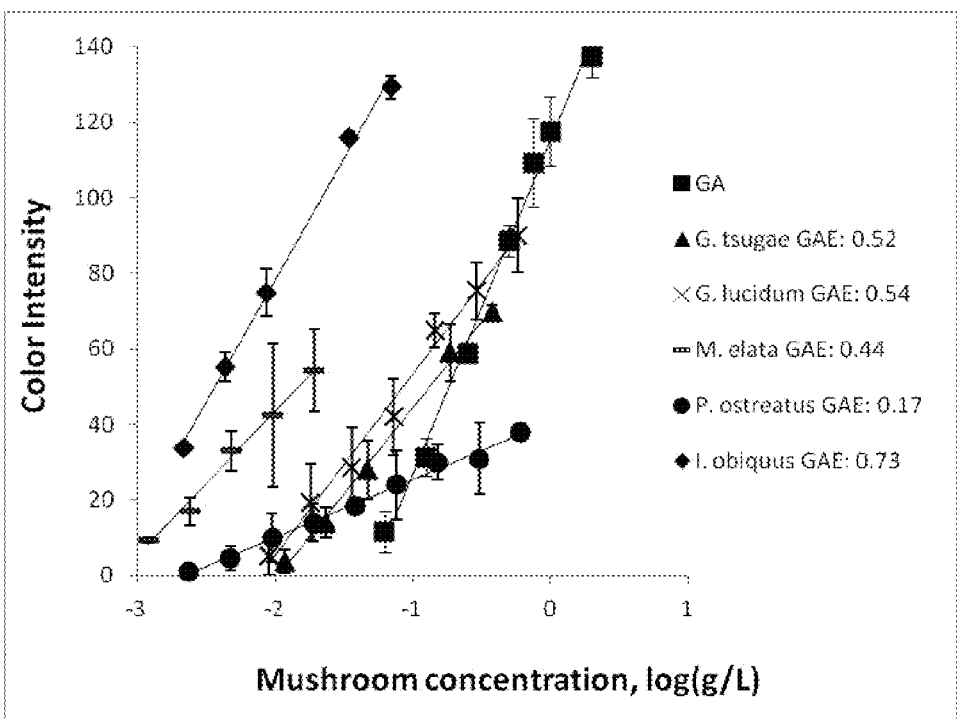

FIG. 4 contains calibration curves of the blue color intensity of ceria paper sensors as a function of antioxidant concentration according to an embodiment;

FIG. 5 is a table of antioxidant structures, with circled sites indicating the position of the possible location of oxidation and binding sites to the particles;

FIG. 6 is a graph of colorimetric responses of sensors prepared with various types of ceria (4%) after addition of 500 ppm CA (from left to right: 1—Sigma-Aldrich, #289744, 10-20 nm (20% colloidal dispersion in aqueous acetic acid (2.5%)); 2—Alfa Aesar, #40125, 10-20 nm (20% in $H_2O$, colloidal dispersion stabilized in 0.4 M acetate); 3—Alfa Aesar, 5 nm, (17% aq in citrate); 4—SkySpring, #2810NH, 10-30 nm; 5—Sigma, #MKBB9545, 25 nm; 6—Sigma, #166D13H, 25 nm; 7—200 nm);

FIG. 7 is a graph of a calibration curve showing blue color intensity of ceria paper sensors as an indirect function of ascorbic acid concentration (color reduction by surface adsorbed peroxyl radical scavenging onto treated ceria NPs);

FIG. 8 is a graph depicting linear correlations of blue color intensity as a function of the log of the concentration for five medicinal mushroom samples, where GAE was calculated by comparison of the slope of each line to that of GA, and represented in terms of GAE (mmol GA/g sample); and FIG. 9 is a table summarizing results from application of ceria sensors for the analysis of antioxidant capacity of teas, as well as comparison to results attained using the conventional ORAC assay.

DETAILED DESCRIPTION

Several recent works report development of nanoparticle (NPs) based antioxidant assays that monitor changes in the physicochemical properties of nanoparticles as they interact with antioxidants. The most commonly used strategies are based on gold NPs in which detection of antioxidants is achieved indirectly by monitoring NP aggregation, NP enlargement in the presence of $AuCl_4^-$ and the antioxidant compound, formation of NPs by reduction of gold salts facilitated by antioxidants, or by inhibition of $H_2O_2$-mediated growth of gold nanostructures by antioxidants. Changes in the physicochemical properties of the NPs in contact with antioxidants indicate antioxidant activity in the form of reducing power, which correlates well with the oxidation potential. However, all previous colorimetric NP-based assays for the detection of antioxidants are carried out in colloidal dispersions.

Accordingly, described herein are portable nanoparticle-based methods and assays, which according to one embodiment are similar to a small sensor patch, for the rapid and sensitive detection of antioxidants in food. According to an embodiment, the method and assay is based on the use of immobilized ceria nanoparticles which change color after interaction with antioxidants by means of redox and surface chemistry reactions. Monitoring corresponding optical changes enables sensitive detection of antioxidants in which the nanoceria provides an optical 'signature' of antioxidant power, while the antioxidants act as reducing agents. The sensor has been tested for, for example, detection of common antioxidant compounds including ascorbic acid, gallic acid, vanilic acid, quercetin, caffeic acid, and epigallocatechin gallate and its function has been successfully applied for the assessment of antioxidant activity in real samples (teas and medicinal mushrooms). The colorimetric response is concentration dependent with detection limits ranging from 20-400 μM depending on the antioxidant involved. Steady-state color intensity is achieved within seconds upon addition of antioxidants. According to one embodiment, the results can be presented in terms of Gallic Acid Equivalents (GAE), although other reporting mechanisms are possible. The results obtained by the method or assay, quantified in terms of GAE, can also be compared with those obtained using commonly accepted antioxidant assays. The sensor performs favorably when compared with commonly used antioxidant detection methods. The methods and assays are particularly appealing for remote sensing applications where specialized equipment is not available, and also for high throughput analysis of a large number of samples. There are also numerous potential applications for antioxidant detection in remote locations and developing countries.

According to one embodiment is a fully-integrated colorimetric assay in which immobilized NPs of cerium oxide ($CeO_2$ or nanoceria) are used as color indicators. Due to the dual reversible oxidation state of cerium Ce(III)/Ce(IV) on the NP surface, nanoceria has the ability to change redox states and surface properties when in contact with antioxidants. These changes are accompanied by a color change that is used in this work to assess the total antioxidant capacity. To fabricate the sensor, ceria NPs are attached onto filter paper or another suitable surface in order to create an active ceria-based sensing platform that provides a colorimetric readout, and is inexpensive and easy-to-use. Introduction of antioxidant samples to the ceria sensor induces a color change that is proportional to the antioxidant concentration of the sample. The assay does not require reagents (except for the sample), specialized equipment or the use of an external power supply. The nanoceria assay can be used independently or in conjunction with current procedures (FRAP, CUPRAC, Au NPs reduction, ORAC, TEAC, TRAP, or DPPH) to more comprehensively assess antioxidant activity.

According to an embodiment are two antioxidant detection mechanisms using immobilized ceria NPs. One strategy relies on the ability of antioxidant compounds to reduce cerium on the NP surface from Ce(IV) to Ce(III). This strategy takes advantage of coexistent dual Ce(IV/III) oxidation states on the NP surface. This process is dependent on the concentration of the reducing/antioxidant compound and is accompanied by a color change that is specific to the type of antioxidant and proportional to its concentration. Soluble Ce(IV) ions (e.g. cerium sulfate in sulfuric acid solution) are known powerful oxidizing agents. However, studies on the potential use of colloidal ceria NPs as an oxidizer and colorimetric agent for the detection of antioxidants have not been reported. Monitoring the corresponding optical changes in the ceria NPs enables sensitive detection of antioxidants in which the nanoceria provides an optical 'signature' of antioxidant power, while antioxidants themselves, act as reducing agents. To exemplify, a redox reaction between $CeO_2$ and a common antioxidant (ascorbic acid as an example) is:

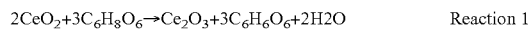
$2CeO_2+3C_6H_8O_6 \rightarrow Ce_2O_3+3C_6H_6O_6+2H_2O$  Reaction 1

A second method indirectly quantifies the ability of antioxidants to scavenge surface adsorbed peroxyl radicals residing on pre-treated ceria NPs. Formation of surface adsorbed ceria-peroxyl complexes on ceria particles treated with $H_2O_2$ has been reported. This process occurs concomitantly with a color change from white/yellow to dark brown (Ce—OOH complexes). In this assay, addition of antioxidants causes a decrease in color intensity of the cerium complex in a concentration dependent manner. This principle was used as an indirect color inhibition method for assessing antioxidant power through inactivation of surface adsorbed superoxides.

Examples

Reagents and Equipment

Cerium (IV) oxide nanoparticles, or ceria 20 wt. % colloidal dispersion in 2.5% acetic acid, 10-20 nm (289744) average particle size, hydrogen peroxide and sodium phosphate were from Sigma Aldrich. The average particle size of the 10-20 nm ceria nanoparticles was verified by scanning electron microscopy (SEM) and particle size distribution (PSD). Filter paper (P5; medium porosity; slow flow rate) was purchased from Fisher Scientific and used as received. All reagents were used without further purification and all solutions were prepared with distilled, deionized water (Millipore, Direct-Q system) with a resistivity of 18.2 MΩ. Fluorescein sodium salt, and [2,2'-azobis(2-amidino-propane) dihydrochloride (AAPH) were from Fisher Scientific. The antioxidants 6-Hydroxy-2,5,7,8-tetra-methylchroman-2-carboxylic acid (Trolox), and epigallocatechin gallate (EGCG) were from Sigma Aldrich; L-ascorbic acid (AA), and gallic acid (GA) were from Acros; vanillic acid (VA) and quercetin (Q) were from Alfa Aesar; and caffeic acid (CA) was from Spectrum Chemical. Teas, *Camellia Sinensis* (tea), and *Aspalathus linearus* (rooibos) were attained from PCC Natural Market in Seattle, Wash. in commercial form from Choice Teas, and also from the Potsdam, N.Y. Food Co-op, sold as individually packaged loose leaf teas. Medicinal mushrooms were obtained from biologist Colden McClurg; *Ganoderma lucidum* (reishi) was purchased at a farmer's market in Seattle, Wash. in fall 2011; and *Ganoderma tsugae* (reishi) was harvested in Trumansburg, N.Y. in late July 2012; *Morchella elata* (morel) was harvested in mid June 2012 in the Bitterroot National Forest Montana, following a forest fire in September 2011, and *Pleurotus ostreatus* (oyster) were harvested at Allen's Falls, Potsdam, N.Y. in late July 2012. *Inonotus obiquus* (chaga) was obtained by Mike Perry and harvested in the northern Adirondack Mountains in early April 2012.

UV-VIS spectrophotometric tests to monitor the spectral properties of nanoceria in the presence of antioxidants were carried out with a Shimadzu P2041 spectrophotometer equipped with a 1-cm path length cell. A fluorescence 96 well plate reader (Gemini EM fluorescence plate reader by Molecular Devices) was used to perform the ORAC assay for validation and inter-assay comparison purposes.

Fabrication of a Ceria Sensor

To prepare the ceria sensor, round-cut 11 cm Fisher filter paper disks were soaked in 4% cerium oxide in distilled water, and dried at 85 C for 5 minutes. Dried ceria papers were cut with a %2" hole-puncher into 0.67 mm diameter circular discs. Although many of the embodiments described herein utilize filter paper and circular discs, numerous other embodiments are possible and have been envisioned. For example, many other types of surfaces and/or materials can be utilized to hold the NPs. Further, these surfaces and/or materials can be any shape. Essentially any surface, material, or shape is possible as long as the ceria detection is maintained.

Colorimetric Measurements

Direct Nanoceria Reduction Procedure.

The direct assay was carried out by applying antioxidant solutions in concentrations ranging from 0.008 to 100 mM in 20 μL aliquots to ceria paper discs. The samples were allowed to dry on the paper. The disks were then attached to the back of a sticker for color visibility, organization and ease of sample handling, and scanned for color analysis. Calibrations were made for each antioxidant showing the direct relationship between blue color intensity and concentration.

Indirect Assay: Peroxyl Radical Scavenging.

The ability of an antioxidant to scavenge peroxyl radicals was quantified as % yellow color inhibition, indicating the peroxyl radical scavenging capacity of an antioxidant against surface adsorbed Ce—OOH complexes. To induce formation of peroxyl complexes, the immobilized ceria was first treated with hydrogen peroxide. For this, 20 μL of 0.55 M hydrogen peroxide was added to each paper disc, which was then rinsed with water to remove excess $H_2O_2$ and allowed to dry for 30 minutes on filter paper. After pre-treatment, 20 μL of antioxidant solution of various concentrations was applied to each disc. After reaction with antioxidants, the ceria discs were scanned and analyzed for % color inhibition. A calibration was created for each antioxidant showing the direct relationship between color intensity and concentration.

Data Analysis

Sensors were scanned in color photo setting 200 dpi using an HP Scanjet Scanner and saved as JPEG images, which were imported into Adobe Photoshop and analyzed using the eyedropper tool. Images of AA were analyzed using RGB, CMYK, greyscale and Lab color intensities; all of which were graphed vs. concentration in order to determine the most sensitive and accurate method of analysis. Analysis using the blue (B) color channel allowed for detection of lowest concentrations with greatest sensitivity and linearity of all color analysis options and thus all calibrations were created using blue color intensity. Antioxidant activity is presented in units of gallic acid equivalence (GAE), noted as mM GA with equivalent activity to 1 mM sample, determined from the ratio of slopes ($m_{sample}/m_{Gallic\ acid}$).

Validation and Interassay Comparisons

To validate the ceria sensors, the ORAC assay was selected to perform interassay comparison, and determine the relative antioxidant capacity of real samples. The ORAC assay was selected as this method has been adopted by the US Department of Agriculture (USDA), as its major antioxidant assay for quantification of the health benefits of a variety of foods. The ORAC assay was carried out using guidelines from Zen-Bio Laboratories and Henning. For this, 75 μL of 1.9 μM fluorescein, in a 75 mM sodium acetate buffer (pH 5.44) were added to each well of a 96 well plate, followed by 50 μL of samples: antioxidants (0.01-50 μM), tea (0.08 mg/mL), Trolox control (50 μM) or buffer as a blank. The plate was incubated for 10-20 minutes at 37° C. and then 240 mM AAPH oxidant (2,2'-azobis(amidinopropane)dihydrochloride) was added using a multiwell pipette to initiate the reaction. A kinetic assay was performed for 90 minutes with readings taken every minute. The quenching of fluorescein emission peak by AAPH was monitored at an excitation and emission wavelengths set to 485 nm and 538 nm, respectively, and antioxidant protection was assessed and given an ORAC value. The ORAC value was calculated by finding the net area under the curve (net AUC) of each sample: (AUC sample-AUC blank). The net AUC provided by each sample was compared to that provided by Trolox, revealing antioxidant strength in terms of mmol Trolox/g sample. The equation used was (net $AUC_{sample}$/net $AUC_{Trolox}$)*(mmol Trolox/g sample).

Analysis of Samples

Four varieties of tea (*Camellia sinensis* teas (green, black and white), and herbal tea, *Aspalathus linearus* (Rooibos)) from the same distributor (Choice Teas) were brewed under the same conditions (2 g tea/200 mL water, 80° C., 5 minute brew). To determine TEAC using the ORAC assay, all samples were diluted to appropriate concentrations. For the analysis, 0.08 g/L samples of all four teas were tested side by side along with 50 μM Trolox as the standard and buffer as the blank. For GAE determination, 1:1 serial dilutions of each sample were prepared and applied to ceria sensors. After drying, sensors were analyzed as described above, and a linear calibration (color intensity vs. concentration (g/L)) was created for each sample. The slope (m) of this correlation was compared to that of gallic acid ($m_{sample}/m_{GA}$) to determine GAE (mmol GA/g sample). GAEs were determined, as well for five types of medicinal mushrooms (*Ganoderma tsugae* and *lucidum* (Reishi), *Morchella elata* (Morel), *Pleurotus ostreatus* (oyster), and *Inonotus obiquus* (chaga). Each sample of mushroom was finely chopped and simmered for 2 hours. The resulting volume of solution was used to calculate concentration of the final solution (g sample/mL final solution). Samples were analyzed following the same procedure as was used in tea analysis.

Figure 1A:
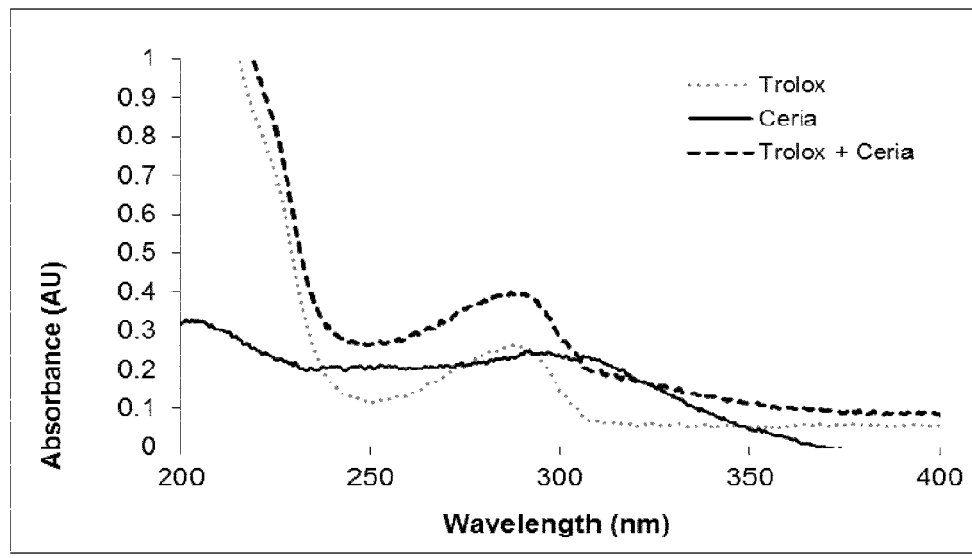
FIGS. 1A and 1B are graphs of UV-VIS spectra of ceria NPs dispersion (13 ppm) in the presence and absence of selected antioxidants according to an embodiment: trolox (FIG. 1A, top), gallic acid (FIG. 1A, bottom) and ascorbic acid (FIG. 1B, top), vanillic acid (FIG. 1B, bottom) as compared to the spectra of the antioxidant in the absence of ceria.
Figure 1A:
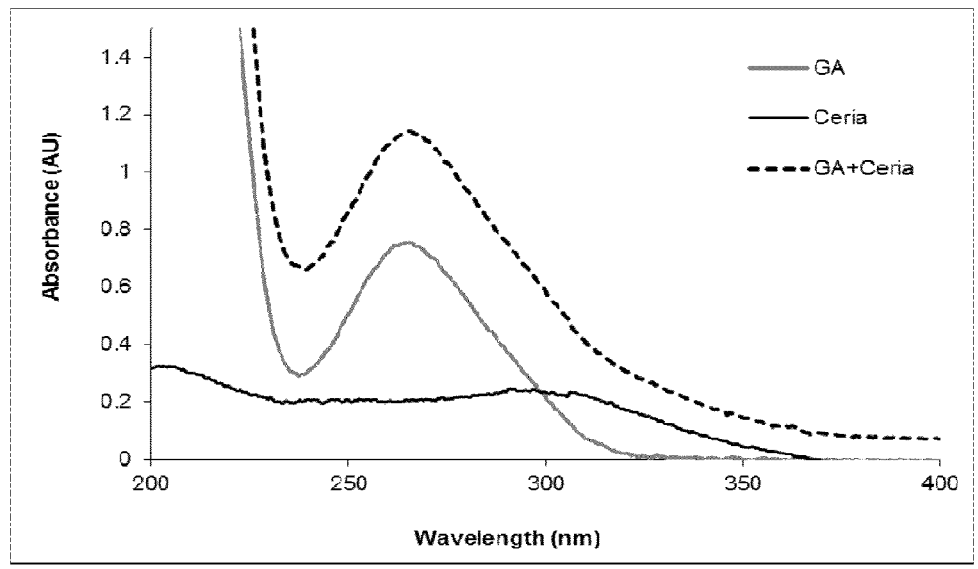
Figure 1B:
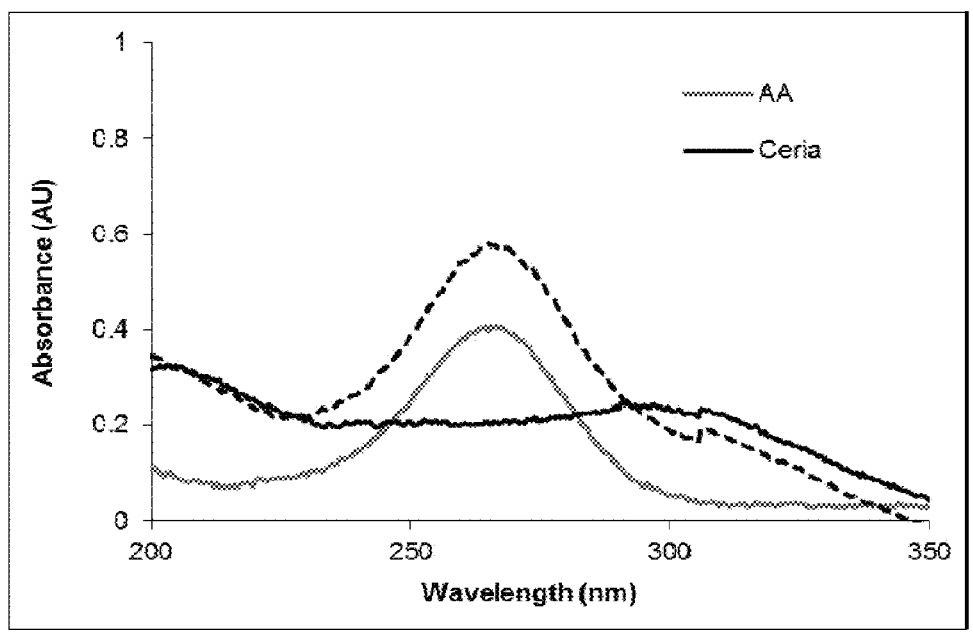
Figure 1B:
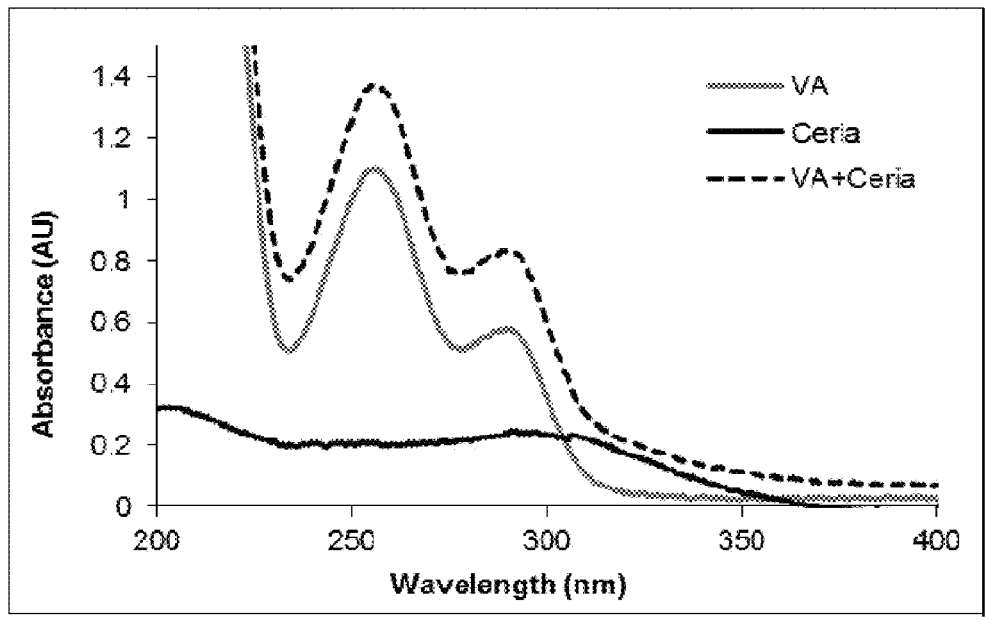
Figure 2:
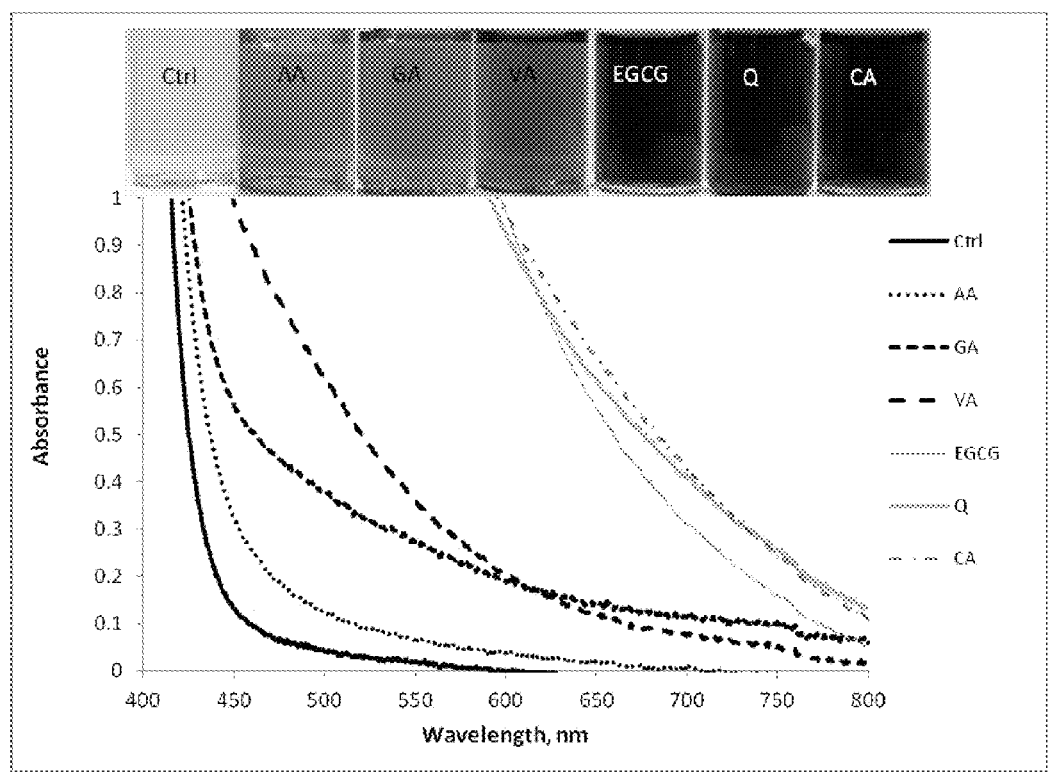
FIG. 2 is a graph of UV-VIS responses of a ceria NPs dispersion before and after addition of antioxidants (all antioxidants present at 0.5 mM in 2% ceria solutions), as well as images of vials which represent (from left to right) the samples shown in the legend (from top to bottom)

Spectroscopic Investigation of Ceria NPs Dispersions in the Presence of Antioxidants UV-VIS spectroscopy on colloidal dispersions was used to study whether interaction of ceria NPs with antioxidants in solution induces spectral changes of ceria and if the color change is concentration dependent. A series of six antioxidants were tested, Trolox, EGCG, AA, GA, VA and CA, while the NPs concentration was varied from 0.013 to 20% w/v. Absorption spectra of ceria NPs at a concentration of 0.013% shows a distinctive peak with a maximum at ~300 nm corresponding to the band gap of $CeO_2$ due to the charge transfer between $O_{2p}$ and $Ce_{4f}$ in $O_2^-$ and $Ce^{4+}$.[26] Addition of antioxidants to this dispersion increased the maximum absorption peak of the antioxidants, as shown in FIGS. 1A and 1B. This indicates an enhancement in the UV absorption behavior and might be due to oxidation of the antioxidants by ceria. This is consistent with previous observations that ceria acts as an oxidizing agent in the oxidation of organic compounds, an observation that was associated in some reports with an 'oxidase-like' mimetic activity. When much higher concentrations of ceria (>2%) were tested, addition of antioxidants induced a strong almost instantaneous visual color change of the colloidal solution from colorless to dark brown for all six antioxidants tested. FIG. 2 shows the corresponding absorption spectra of a series of ceria NPs dispersions in the absence and presence of antioxidants. As can be seen, addition of antioxidants induced a strong red shift in the absorption spectra of ceria. The magnitude of the red shift and the intensity of the color varies with the type of antioxidant. The spectral changes indicate alterations in the composition, structure or physico-chemical properties of the ceria NPs' surface induced by the presence of antioxidants. The observed red shift is similar with that reported previously in studies of the interaction of titania NPs with catechol-type derivatives, that suggested formation of charge transfer complexes between the semiconductor and catechol. These charge transfer complexes have shown significantly improved optical and charge separation properties explained by a charge transfer of electrons from the catechol-type ligands into the conduction band of titania.

Studies of the interaction of ceria with catecholate compounds have not been reported. It is possible that the dual Ce(IV)/Ce(III) oxidation states in ceria and the strong oxidising ability of these particles contribute to the overall process. The proposed mechanism involves partial reduction of the ceria surface from Ce(IV) to Ce(III) which occurs with concomitant oxidation of the antioxidants (Reaction 1 as an example for AA). The oxidation compounds and reaction intermediates have high reactivity. Some of these compounds are quinoid type, involving a number of highly reactive phenoxyl radicals derived from the catecholic structure of an antioxidant. As a result of their reactivity, either the parent compound or the oxidation products can bind to the OH-rich particles and self-assemble around the particle, generating charge transfer ceria-antioxidant complexes, or antioxidant modified ceria NPs, that possess distinct spectral and electronic properties as compared with the bare ceria or the parent antioxidant. Since the color change is indicative of the reducing power of the antioxidant and their binding ability to the ceria NPs surface by means of surface chemical reactions, these changes can be used to assess the antioxidant capacity. The results in FIG. 2 show a possible correlation of the color intensity with the chemical structure and the binding ability of the antioxidants. The lowest shift was observed for AA, which lacks the catecholate structure, but contains four hydroxyl groups that could participate in binding to the ceria particles. The next two compounds, GA and VA have a phenolic acid structure with three and one OH groups, respectively, on the phenolic ring. Both can form o-substituted quinones and have higher reactivity than AA due to potential formation of phenoxyl intermediates. In the same order, EGCG, Q and CA show a greater red shift and the strongest color intensity. Structurally, these compounds have increased reactivity likely due to their large number of OH functional groups, many of which are o-substituted, allowing them to function as a "claw-like" structure during reaction with ceria NPs.

Figure 3:
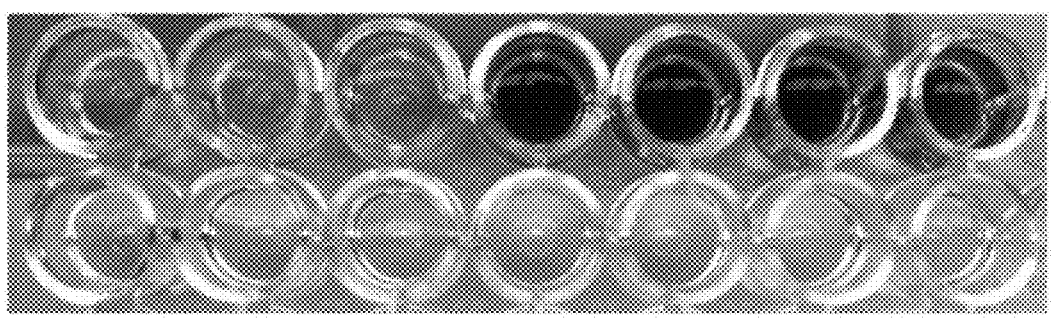
FIG. 3 is an image depicting the effect of ceria concentration on color formation in the absence (bottom row) and presence of 0.45 mM caffeic acid (top row), where ceria concentrations 25, 50, 100, 1000, 10K, 20K, 40K ppm (left to right)

The spectroscopic studies indicate that a visible color change, or formation of charge transfer complexes, is only observed when ceria NPs are used at high concentrations (e.g. 2% as shown in FIG. 2). FIG. 3 shows color changes of ceria NPs dispersions of increasing concentrations in the presence and absence of 0.45 mM caffeic acid. Similar color changes were observed for the other antioxidants tested. Thus, the use of high concentrations of ceria is required to develop a ceria based analytical method for the detection of antioxidants with adequate sensitivity. While the assay can be performed in colloidal ceria dispersions, we aim in this work to fabricate portable self-integrated ceria sensors, as described in the following section.

Development and Analytical Characterization of the Ceria Based Paper Assay with Direct Color Quantification Further experiments were performed with ceria NPs immobilized onto filter paper, effectively constituting the sensing platform for the detection of antioxidants. Attachment of the particles onto the paper surface was achieved by surface adsorption. The particles are stabilized through the formation of hydrogen bonding between the OH-rich ceria surface and the cellulosic fibers. The proof-of-concept for this ceria sensor was demonstrated through detection of six antioxidant compounds. The operational conditions and analytical performance characteristics including detection limit, sensitivity, reproducibility and linearity were established. FIG. 4 displays the colorimetric responses of the ceria paper to addition of increasing concentrations of antioxidants and the corresponding calibration curves. The color intensity is linearly dependent on the antioxidant concentration for all tested antioxidants. The color changes of the immobilized ceria on paper indicate surface chemistry reactions that are similar to those observed in colloidal suspensions. The intensity of color is dependent on the type of antioxidant and varies with reducing capacity of Ce(IV) to Ce(III) as well as with the binding ability of each antioxidant (or their oxidation products) to the ceria surface. Therefore the color formed and consequently the sensitivity of these sensors is dependent on the oxidation potential and the chemical structure (e.g. the size, position and number of the OH substituents) of the antioxidants.

TABLE 1 summarizes the analytical performance characteristics of ceria paper for the detection of the antioxidants and ranks their reducing capacity quantified using the sensitivity of each calibration curve. For comparison with conventional antioxidant tests, the reducing ability of each antioxidant used in the ceria assay is presented in terms of GAE or mM GA with equal ceria reducing power to 1 mM sample. GAE is a commonly used method of representing relative antioxidant strength, as is seen in methods such as the Folin Ciocalteau spectroscopic assay. This term relates the antioxidant strength (electron donating capacity, ROS scavenging capacity, etc.) of one compound to another by relating it to GA as a common standard. The GAE was calculated by dividing the slope of each antioxidant calibration curve by that of GA. In an attempt to correlate sensor response with chemical reactivity and structure, TABLE 1 compares the antioxidant activity quantified by the ceria sensor with the oxidation potentials of the tested antioxidants, and relates these finding to the chemical structure of each antioxidant. The binding ratio of the antioxidant to the ceria particles has been estimated through UV-Vis studies monitoring the formation of binding complexes in colloidal 2% ceria solutions of with each antioxidant.

TABLE 1

Analytical Performance Characteristics of Ceria Paper

| Antioxidant | Class of Polyphenol | Oxidation Potential | Ceria Sensor GAE | Ceria sensor Sensitivity/LOD | Binding Ratio (Ceria: AOX) |
| --- | --- | --- | --- | --- | --- |
| EGCG | Flavonoids: Flavanols (monomeric: epicatechin (cis)/catechin (trans); polymeric: procyanidins) | 0.19 (solid) 0.12 | 0.7 | 58.176/0.02 | 1:>8 |
| AA | Antioxidant used to protect oxidation of polyphenols. | 0.13 | 1.1 | 97.22/0.4 | 1:31 ± 2 |
| GA | Phenolic Acids: Benzoic Acids | 0.2 | 1 | 88.18/0.05 | 1:>8 |
| Quercetin | Flavonoids: Flavonols | 0.14 | 0.9 | 76.757/0.04 | 1:>3 |
| CA | Phenolic Acids: Cinnamic Acids | 0.2 | 0.7 | 59.303/0.04 | 1:8 ± 3 |
| VA | Phenolic Acids: Benzoic Acids | 0.6 0.06 (solid) | 0.3 | 30.716/0.03 | 1:20 ± 7 |
| Cerium (III) | | 1.44 | — | — | |

It is speculated that the optimum color formation is reached when all ceria has been reduced, and the binding sites have been occupied by the antioxidant. The rate at which this occurs (color intensity vs. concentration of antioxidant added) can be related to the binding affinity or electron donating capacity of each antioxidant toward ceria. This assumption allows comparison of antioxidants to one another in terms of slope or sensitivity. Other factors such as size of the antioxidant and the position of the OH groups may influence sensor response. For example, a high GAE was obtained for EGCG which has the highest number of OH (8) and the lowest oxidation potential. In general, we observed that the GAE varied with the number of OH groups in this order: EGCG (8OH)>AA (4OH)>GA (4OH)>Q (5)>CA (3OH)>VA (2OH). This trend is consistent to that reported previously with other antioxidant assays. Significant differences were noticed in the linearity range and binding ratio, which appears to be related to the size and position of OH groups within the molecule. For example, while having a high GAE, the EGCG shows the lowest limit of linearity (LOL), which can be due to the large size of the molecule. When EGCG was compared with GA, which has a similar catecholic type reactive group but a significantly smaller size, it was found that GA had a wider linear response range. Significantly wider linearity ranges were obtained for smaller molecules like AA and VA. Within the group of antioxidants tested, the orientation of nucleophillic groups (—OH, and —OCH3) appears to have a strong effect on GAE. This parameter may override the effect of size on GE. TABLE 1 shows that those antioxidants which contain 3 consecutive ortho-OH groups have the highest GAE, and those without ortho-OH groups have the lowest. The location of nucleophillic groups on the ring also determines the reactivity (ceria reduction) and the surface modifications of the NPs. The higher reactivity of ortho conformations is consistent with antioxidant activity trends reported in previous works.

TABLE 2 compares the ranking of antioxidant capacity in terms of GAE quantified with the ceria sensors to those reported with conventional antioxidant assays. Ceria sensors rank antioxidants in similar order to the commonly used assays, indicating that this is a valid method of analysis. It is particularly interesting to note that the other assays, which involve reduction of a redox metal (FRAP and CUPRAC), show the most similar rankings of antioxidants, indicating that a similar mechanism may be involved. These results show good correlation between the ceria sensor and the other antioxidant assays.

TABLE 2

Ranking of Antioxidant Capacity

| | Ceria Sensors | FRAP | CUPRAC | ABTS | Folin Ciocalteau |
|---|---|---|---|---|---|
| Principle | Nanoceria surface reduction ($Ce^{4+}/Ce^{3+}$) | $Fe^{3+}$ Reduction | $Cu^{2+}$ Reduction | Radical Scavenging | Electron Donation |
| EGCG | 1 | 1 | 1 | 1 | 1 |
| Gallic Acid | 2 | 2 | 3 | 2 | 4 |
| Caffeic Acid | 3 | 3 | 2 | 3 | 2 |
| Ascorbic Acid | 4 | 4 | 5 | 5 | 5 |
| Vanillic Acid | 5 | NA | 4 | 4 | 3 |

Study of Reproducibility, Robustness and Stability of the Ceria Based Assay

The reproducibility of the assay was evaluated for 15 identical ceria paper sensors, prepared following an identical experimental procedure. The average color intensity after addition of 5 mM CA was 125(±5) for n=15 paper sensors with a calculated R.S.D. value of 4%, which demonstrate that the assay is highly reproducible. When this color intensity was used along with the CA calibration curve (see FIG. 4) to confirm CA concentration, mM CA was revealed to be 5.9±1.7 mM showing the reproducible applicability of this assay for analysis of real unknown samples.

Due to the nature of the inorganic material constituents (ceria NPs are stable for years at room temperature) these sensors are extremely robust and do not require special storage or temperature conditions. This is a clear advantage over conventional assays, all of which involve the use of sensitive enzyme and colorimetric dyes.

It is well known that surface reactivity varies with the synthetic procedure and additives/surface coatings used to stabilize the particles. To test the robustness of the assay when same size ceria NPs particles (average diameter ~20 nm as reported by the provider) were purchased from different suppliers, we have performed reproducibility tests with the sensors fabricated in the same conditions but using different types of NPs. Colloidal nanopowders and liquid dispersions were used in these assays. In general, all particles provided quantifiable color change but the intensity of the color varied among the different particle tested (see FIG. 6). Aqueous suspensions (stabilized in acetic acid or citrate solutions—as reported by the supplier) provided the best reproducibility, uniformity, and the highest colorimetric response on the paper platform. Therefore, the highest reproducibility and sensitivity was achieved with these particles. It is possible that the acetate and citrate stabilizers participate in the binding of the antioxidants through the surface exposed citrate or acetate groups. In contrast, dry nanopowders showed poor NP distribution on the paper, a relatively large standard deviation and significantly lower color intensity. This is likely due to formation of aggregates upon dispersion in the aqueous solution, potentially related to absence of stabilizer agents. To assess the effect of NPs size, particles of 5 and 200 nm were also tested. Both yielded a visual color change; the largest particles gave a lower response as expected, due to lower surface area to volume ratio. However, no significant difference was observed between the 5 and 20 nm particles.

Indirect Assay

In the indirect assay, the ability of the antioxidant to scavenge surface adsorbed peroxyl radicals was colorimetrically determined by quantifying the ability of the antioxidants to inactivate these radicals from the ceria NPs surface. Surface adsorbed peroxyl groups were produced by pre-treatment of ceria with hydrogen peroxide, a marker of oxidative stress, which creates a yellow colored complex (Ce—OOH) upon reaction with ceria. Addition of antioxidants to hydrogen peroxide treated ceria paper inactivates these peroxyl groups decreasing the yellow color intensity. Thus, the color inhibition response can be related to the amount of antioxidant added. The ability of an antioxidant to scavenge peroxyl radicals was quantified as % yellow color inhibition, indicating the peroxyl radical scavenging capacity of an antioxidant, which causes the decomposition of yellow Ce—OOH complexes. Since the sensor is based on color inhibition, this method is referred to as an 'indirect' quantification assay. While the concept of color inhibition due to peroxyl radical scavenging by antioxidants is a promising concept for this assay, AA was the only antioxidant, of the six tested, to display this ability in a quantifiable and reproducible fashion, with a distinct decrease in yellow color intensity in direct relation to antioxidant concentration. The decrease in color was observed for AA concentrations between 0.01 and 1.5 mM (FIG. 7), in a much lower concentration range than that obtained with the direct assay. When low concentration of the other antioxidants were added to the treated ceria paper, the yellow color did not show a concentration dependent decrease, while when higher concentrations were used, the paper turned pink/brownish due to the binding of these compounds onto the immobilized particles as described in the direct assay. AA is the only antioxidant among the six without a catecholic ring in its structure, possibly having a greater peroxyl radical scavenging than it has for ceria reduction. It is concluded that while the indirect method does provide some quantifiable results and lower detection limits, the method is generally not applicable to all antioxidants and it is poorly reproducible. Therefore, only the ceria sensors with direct detection have been applied for the analysis of real samples. A comparison of the performance of two methods is presented in TABLE 3.

TABLE 3

Comparison of direct and indirect methods of ceria based sensors

|  | Ease of use | Response time | Accuracy/ Reproducibility | Sensitivity | Recyclability | Range (mM) |
|---|---|---|---|---|---|---|
| Direct | ++ (no pre-treatment) | ++ (immediate) | ++ | ++ | − | 0.3-6 |
| Indirect | + | − | − | + | + | .01-1.5 |

Analysis of Samples

The direct method of analysis was used to analyze the antioxidant capacity of aqueous extracts of several teas and medicinal mushrooms. Choice brand white, and green teas as well as loose leaf black and rooibos teas and tisanes were brewed and compared to one another in triplicate to determine GAE values for Ce(IV) reduction. The results were compared to those obtained from analysis of the Choice brand of all four teas, using an USDA accepted assay, the ORAC assay based on peroxyl radical scavenging capacity. FIG. 8 summarizes results from the application of the ceria sensors for the analysis of antioxidant capacity of teas, as well as comparison to results attained using the conventional ORAC assay. The sensor results follow a similar trend with the ORAC assay, demonstrating good correlation between the new assay and the conventional assay.

FIG. 9 displays results of analysis of five varieties of medicinal mushrooms, including Reishi, "the mushroom of immortality" in traditional Chinese medicine (TCM), among others. GAEs are included for each compound. It was found that for two species of Reishi mushrooms, the one with a darker colored fruiting body (*G. lucidums*), which is thought to occur because of increased concentrations of medicinal compounds (such as polyphenols), did show a higher GAE than the other Reishi species, *G. tsugae*. *G. lucidum*, fell just short of the GAE of chaga, a fungi known for its anti-inflammatory properties. Morel and Oyster mushrooms, primarily consumed for dietary rather than medicinal purposes showed lowest antioxidant capacity in accordance to predictions based on medicinal use. Therefore, these results show favorable agreement with antioxidant capacity assumptions based on traditional usage of each plant.

Due to the unique concentration dependant color formation upon each antioxidant's interaction with ceria, these compounds can be potentially identified using the distinct combination of RGB color intensities. This will facilitate determination of unknown samples, both qualitatively and quantitatively using simple tools such as a computer, camera phone or scanner, Adobe Photoshop, and Excel for quick analysis and matching of the sample to its antioxidant profile (mM of an AOX). The system is particularly appealing for analysis of new and unexplored plants, as is demanded by many field researchers.

Accordingly, described is a robust, stable, easy-to-use and inexpensive portable sensor for measuring food antioxidants; similar to a small sensor patch. The platform is based on immobilized ceria NPs that changes color when in contact with antioxidants by means of surface chemistry reactions. The sensor performed favorably when compared with commonly used antioxidant assays. There are a number of commercial antioxidant kits that are used in laboratory settings, none of which are portable. TABLE 4 shows a summary of commonly used assays, analysis time and performance, as compared to the nanoceria sensor described in this work. Typically, these tests involve multiple steps, require radical stabilization, expensive reagents (peroxidase enzymes and indicator dyes), require special storage conditions, and all need spectrophotometric equipment, which limits price and portability.

TABLE 4

Comparison of Oxidant Measurement Methods

| Method | Operational principle | Instrument requirement | Storage | Steps, Time (prep and measure) | Linear Range | Application in Food Science |
|---|---|---|---|---|---|---|
| Nanoceria reduction | Ceria reduction (electron donation & complex formation) | Paper Based Colorimetric Sensor; scanner; Adobe Photoshop | Highly stable for years; RT | 1 step <1 hour | 0.2-9 mM | Antioxidant capacity of dietary sources; ID of antioxidants in solution. |
| ORAC | Peroxyl radical scavenging (H transfer) | Fluorescence 96 well plate | 3 months: Fluorescein: 4 C. AAPH radical generator: −20 C. | 7 steps 2 hours est. | 8 nM-50 uM [7] | Foods, botanicals, nutraceuticals, dietary supplements |
| FRAP | Iron reduction (electron transfer) | UV-Vis Spectrophotometer 96 well plate | TPTZ: 2-8 C. $FeCl_3$: RT | 4 steps 1 hour | 0.1-1 mM | Tea, and vegetable analysis; other dietary sources. |

TABLE 4-continued

Comparison of Oxidant Measurement Methods

| Method | Operational principle | Instrument requirement | Storage | Steps, Time (prep and measure) | Linear Range | Application in Food Science |
|---|---|---|---|---|---|---|
| CUPRAC | Copper reduction (electron donation) | UV-Vis Spectrophotometer; 96 well plate | 6 months; −20 C. | 4 step 2 hours est. | 1uM-1 mM | Total AOX capacity of vegetables; Addition of AOX to juices, teas, etc. |
| Folin Ciolcalteu | Reduction of Phosphomolybdic-Phosphotungstic acid (total reducing capacity) | UV-Vis Spectrophotometer | 4 years or until turns green; RT | 7 steps ~2 hours | uM | Estimation of total phenolics in wine and plant extracts. |
| DPPH | Neutralization of DPPH· (H transfer) | UV-Vis Spectrophotometer | 1 month; 4 C.; dark | 5 steps 2-3 hours | 0.3-1 mM [9] | Screening of potential natural AOXs (grain, juice, etc.) |
| TEAC | ABTS+· radical scavenging | UV-Vis Spectrophotometer 96 well plate | 3 months: ABTS: 4 C. Trolox: −20 C. | 5 steps 1 hours est. | 4-300 uM [8] | Dietary supplements, topical protection, and therapeutics. |

The ceria nanoparticle assay based on the use of robust inorganic chromogens can overcome these limitations. The sensor has a number of advantages including: (1) stability—nanoceria is stable under normal room-temperature conditions, (2) portability—the particles are immobilized and fixed onto a compact small size (0.67 mm) solid platform, (3) cost and ease of quantification: the color change can be quantified visually with the naked eye. (4) Analysis is a single step process, requiring only addition of sample to the sensor strip, without involving additional reagents; quantification does not involve specialized equipment. Cameras which are installed on cellular phones currently do a sufficient job in capturing color intensity as well. (5) The method is sensitive, with performance characteristics comparable with conventional assays. Robustness, ease-of-use, high reproducibility and stability of the assay set these sensors apart among other antioxidant assays that involve sensitive colorimetric dyes and enzymes.

The ease-of-use makes this assay ideal for field explorations for antioxidant containing botanicals. Scientists have previously reported the lack of portable, efficient antioxidant assays for use in remote places such as the jungles of the Niger which contain many medicinal and antioxidant containing botanicals. Commonly used spectrophotometric assays, which require cumbersome laboratory equipment, electricity, and a significant level of training and understanding for proper execution are difficult to be performed in field. There are an estimated 300,000-500,000 plant species on the planet, and only a small percentage have been examined for use as potential drug candidates for prophylaxis and therapy. The high portability of the ceria assay can facilitate field work and advance the search for antioxidant containing botanical medicines.

Because of the multidimensional properties of ceria NPs (dual oxidation state, redox activity, surface functionality), this assay may be the first of several possible ways to utilize these particles to assess antioxidant activity. For example, in the future other tests can be created that utilize the ability of nanoceria to interact with reactive oxygen and nitrogen species to analyze antioxidant capacity. Additionally, because the assay is based on the interaction of ceria with antioxidants, a variety of other antioxidants could be determined. However, further mechanistic investigations of the interaction between antioxidants and ceria, with a study of surface properties, surface coverage and reactivity are needed to fully understand the nature and the origin of the spectral changes and better relate sensor response to antioxidant structure and antioxidant activity.

Although the present invention has been described in connection with a preferred embodiment, it should be understood that modifications, alterations, and additions can be made to the invention without departing from the scope of the invention as defined by the claims.

What is claimed is:

1. A method for the portable colorimetric detection of an antioxidant in a food sample, the method comprising the steps of:
   providing a colorimetric reagent comprising a plurality of ceria nanoparticles immobilized to a support;
   contacting the colorimetric reagent with the food sample; and
   detecting an optical property of the colorimetric reagent, wherein a change in the optical property of the colorimetric reagent is associated with the presence of antioxidant in the food sample, and further wherein the change in the optical property of the colorimetric reagent is dependent upon the concentration of the antioxidant in said food sample.

2. The method of claim 1, wherein the concentration-dependent change in the optical property of the colorimetric reagent is associated with a concentration of approximately 20-400 μM of said antioxidant.

3. The method of claim 1, wherein the plurality of ceria nanoparticles comprise cerium oxide.

4. The method of claim 1, further comprising the step of:
   reusing the colorimetric reagent.

5. The method of claim 1, wherein the plurality of ceria nanoparticles comprise cerium (IV), and further wherein said change in the optical property of the colorimetric reagent is caused by the reduction of said cerium (IV) to cerium (III) caused by the antioxidant in said sample.

6. The method of claim 1, wherein the colorimetric reagent further comprises a plurality of peroxyl radicals complexed with said ceria nanoparticles.

7. The method of claim 1, further comprising the step of:
comparing the optical property of the colorimetric reagent to a pre-determined value.

8. A method for the portable colorimetric detection of an antioxidant in a food sample, the method comprising the steps of:
providing a colorimetric reagent comprising a plurality of ceria nanoparticles immobilized to a support, the plurality of ceria nanoparticles comprising cerium oxide;
contacting the colorimetric reagent with the food sample;
detecting an optical property of the colorimetric reagent, wherein a change in the optical property of the colorimetric reagent is associated with the presence of antioxidant in the food sample, and further wherein the change in the optical property of the colorimetric reagent is dependent upon the concentration of the antioxidant in said food sample; and
comparing the optical property of the colorimetric reagent to a pre-determined value.

9. An assay kit for the portable colorimetric detection of an antioxidant in a food sample, the assay kit comprising a food sample and a colorimetric reagent comprising a plurality of ceria nanoparticles immobilized to a support, wherein the colorimetric reagent comprises an optical property, and further wherein a change in the optical property of the colorimetric reagent is associated with the presence of antioxidant in the food sample, and further wherein the change in the optical property of the colorimetric reagent is dependent upon the concentration of the antioxidant in said food sample.

10. The assay kit of claim 9, wherein the concentration-dependent change in the optical property of the colorimetric reagent is associated with a concentration of approximately 20-400 µM of said antioxidant.

11. The assay kit of claim 9, wherein the plurality of ceria nanoparticles comprise cerium oxide.

12. The assay kit of claim 9, further wherein the colorimetric reagent can be reused for multiple assays.

13. The assay kit of claim 9, wherein the plurality of ceria nanoparticles comprise cerium (IV), and further wherein said change in the optical property of the colorimetric reagent is caused by the reduction of said cerium (IV) to cerium (III) caused by the antioxidant in said sample.

14. The assay kit of claim 9, wherein the colorimetric reagent further comprises a plurality of peroxyl radicals complexed with said ceria nanoparticles.

15. The assay kit of claim 9, wherein the assay kit further comprises means for comparing the optical property of the colorimetric reagent to a pre-determined value.

16. A system for the portable colorimetric detection of an antioxidant in a food sample, the system comprising:
a food sample; and
a colorimetric reagent comprising a plurality of ceria nanoparticles immobilized to a support, wherein the colorimetric reagent comprises an optical property, and further wherein a change in the optical property of the colorimetric reagent is associated with the presence of antioxidant in the food sample, and further wherein the change in the optical property of the colorimetric reagent is dependent upon the concentration of the antioxidant in said food sample.

17. The system of claim 16, wherein the concentration-dependent change in the optical property of the colorimetric reagent is associated with a concentration of approximately 20-400 µM of said antioxidant.

18. The system of claim 16, wherein the plurality of ceria nanoparticles comprise cerium oxide.

19. The system of claim 16, wherein the plurality of ceria nanoparticles comprise cerium (IV), and further wherein said change in the optical property of the colorimetric reagent is caused by the reduction of said cerium (IV) to cerium (III) caused by the antioxidant in said sample.

* * * * *